United States Patent [19]

Knollenberg

[11] Patent Number: 4,893,928
[45] Date of Patent: Jan. 16, 1990

[54] HIGHLY SENSITIVE PARTICLE SIZE DETECTION DEVICE HAVING NOISE CANCELLATION

[75] Inventor: Robert G. Knollenberg, Boulder, Colo.

[73] Assignee: Particle Measuring Systems, Inc., Boulder, Colo.

[21] Appl. No.: 243,988

[22] Filed: Sep. 13, 1988

Related U.S. Application Data

[63] Continuation-in-part of Ser. No. 851,477, Apr. 14, 1986, Pat. No. 4,798,465.

[51] Int. Cl.$^4$ .................. G01N 15/02; G01N 21/53
[52] U.S. Cl. .................................... 356/336; 250/574; 356/343
[58] Field of Search ............... 356/336, 343; 250/564, 250/574, 214 C

[56] References Cited

U.S. PATENT DOCUMENTS

| | | | |
|---|---|---|---|
| 3,822,095 | 7/1974 | Hirschfeld | 356/343 X |
| 3,941,982 | 3/1976 | Knollenberg et al. | |
| 4,173,415 | 11/1979 | Wyatt | 356/343 X |
| 4,571,079 | 2/1986 | Knollenberg | 356/336 |

OTHER PUBLICATIONS

"The Measurement of Particle Sizes Below 0.1 Micrometers", By Robert G. Knollenberg, The Journal of Environmental Sciences, Jan./Feb. 1985.
"Sizing Particles at High Sensitivity in High Molecular Scattering Environments", by Dr. Robert G. Knollenberg, Proceedings—Institute of Environmental Sciences, 1987.

Primary Examiner—Davis L. Willis
Assistant Examiner—Mathew W. Koren
Attorney, Agent, or Firm—Robert E. Harris

[57] ABSTRACT

A detection device is disclosed for determining particle size from particle effected light scattering in a sensing region illuminated by a laser beam and receiving the particles in a medium, such as air. Background light from molecular scattering is reduced to a level that enables light scattered by particles having a size of at least as low as about 0.1 micron to be sensed in a high background of molecular scattering such as, for example, where molecular scattering can exceed the 0.1 micron particle's scattering by one hundred times. High sensitivity at high molecular scattering background is achieved through use of a linear array of detectors positioned, with respect to an imaging system, so that each detector monitors a different portion of the sensing region and provides an electrical output signal indicative of sensed particle presence within that portion monitored, with the output signals from the detectors being parallel processed and with the output signals from detectors monitoring non-adjacent portions of the sensing region being combined at noise cancellation units.

15 Claims, 5 Drawing Sheets

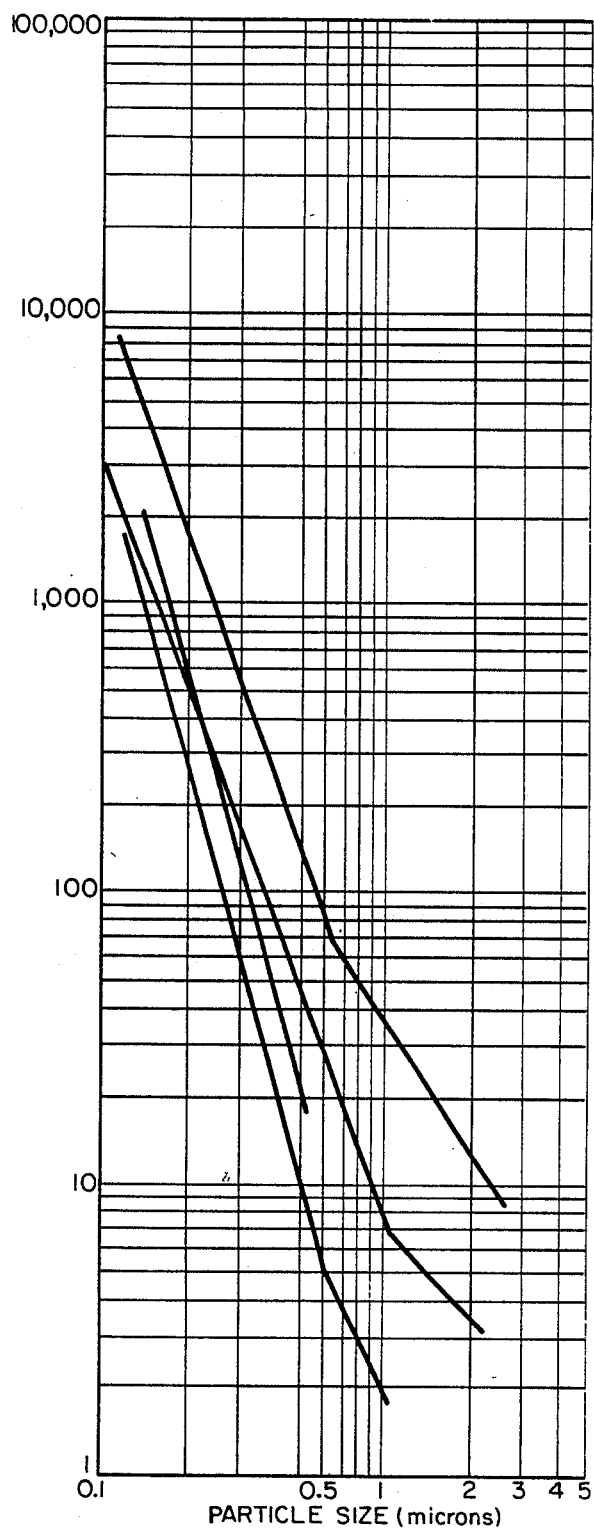
*Fig_3*
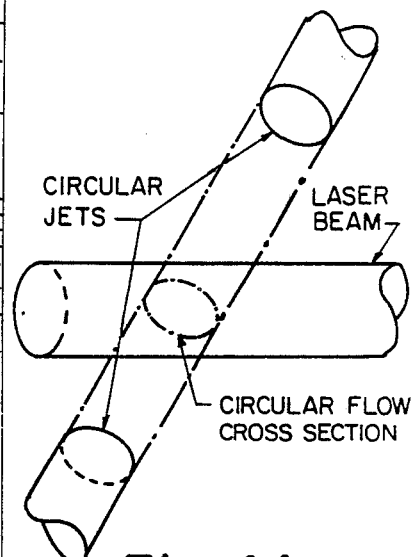
*Fig_4A*
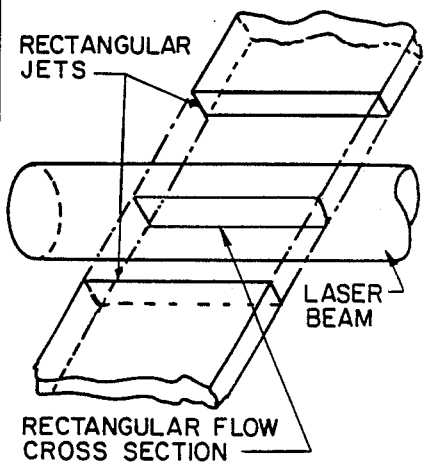
*Fig_4B*

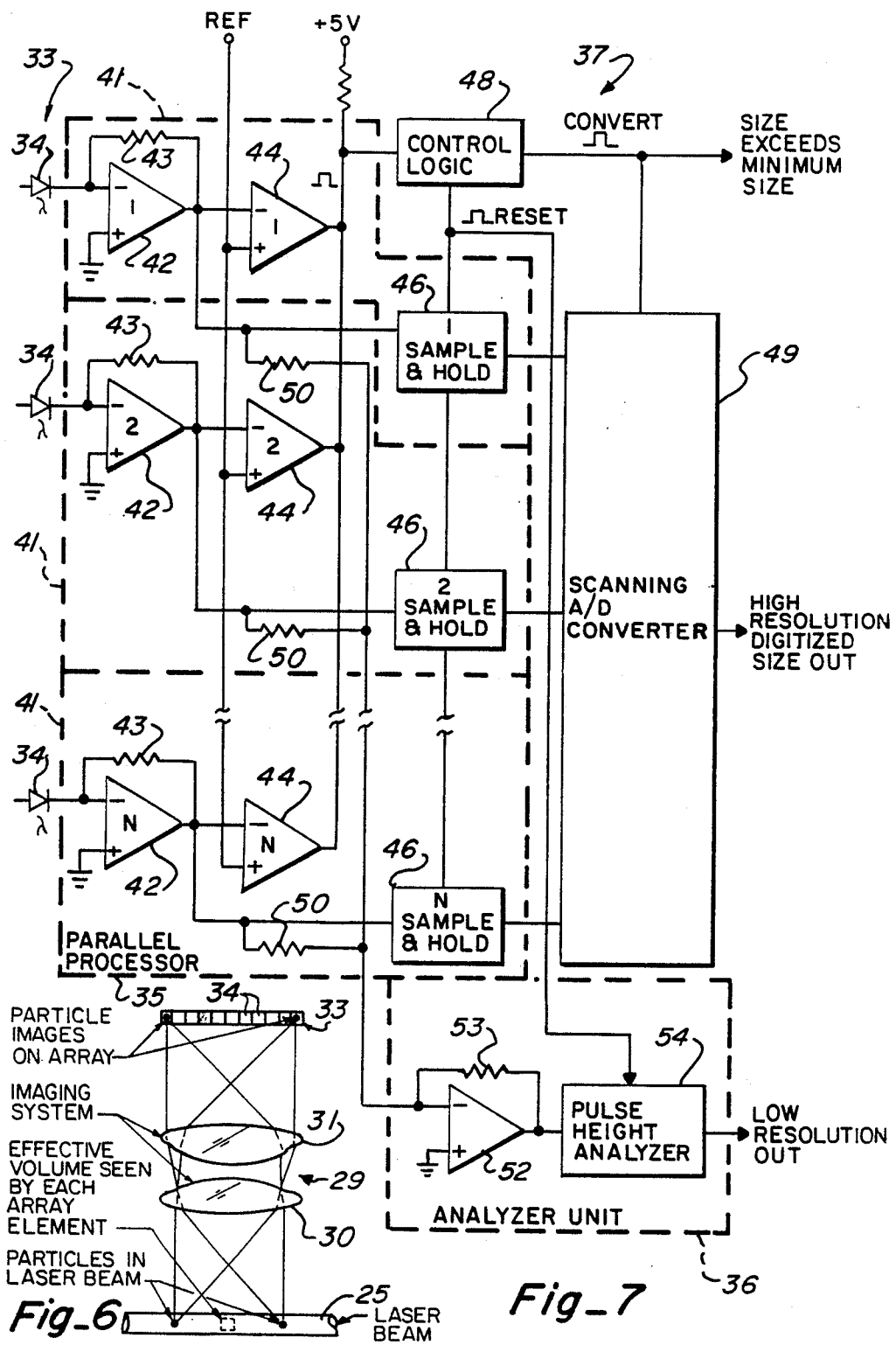

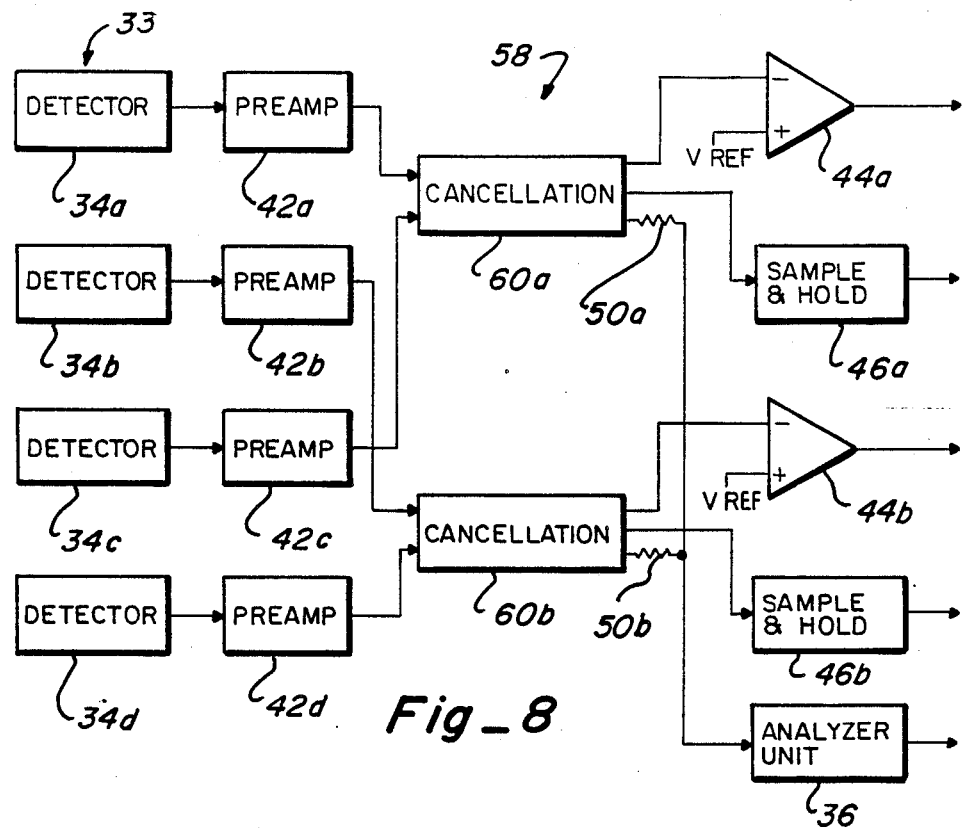
Fig_8
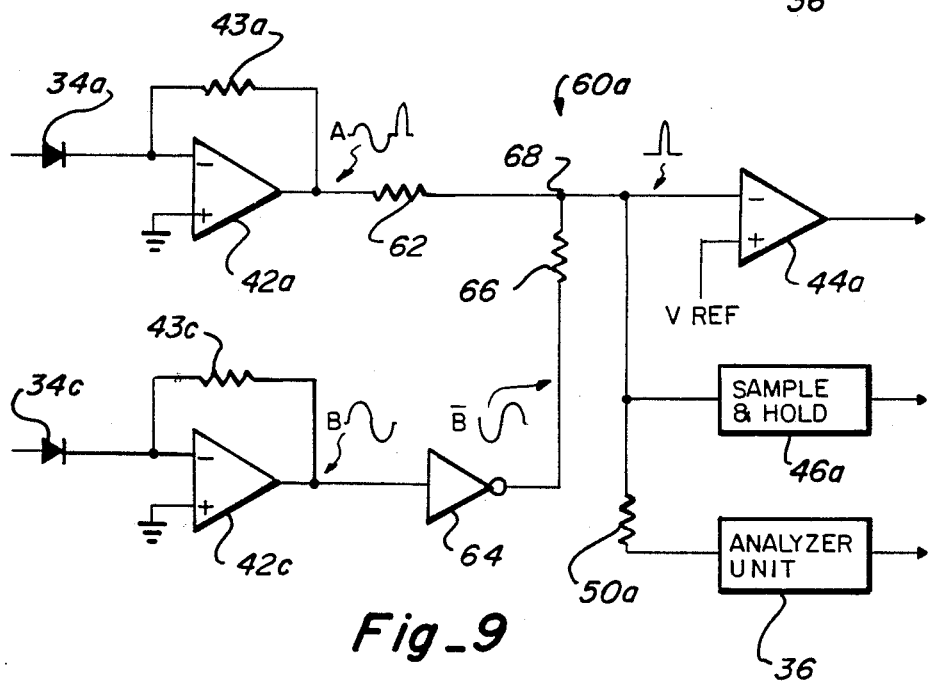
Fig_9

HIGHLY SENSITIVE PARTICLE SIZE DETECTION DEVICE HAVING NOISE CANCELLATION

RELATED APPLICATION

This application is a continuation-in-part of U.S. patent application Ser. No. 851,477, filed Apr. 14, 1986 by Robert G. Knollenberg, entitled "PARTICLE SIZE DETECTION DEVICE HAVING HIGH SENSITIVITY IN HIGH MOLECULAR SCATTERING ENVIRONMENT", and issued Jan. 17, 1989 and U.S. Pat. No. 4,798,465.

FIELD OF THE INVENTION

This invention relates to particle size detection, and, more particularly, relates to particle size detection using light scattering.

BACKGROUND OF THE INVENTION

Devices for determining particle size are now well known, and it is also well known that lasers can be, and have been, heretofore utilized to achieve particle size measurements (see, for example, U.S. Pat. No. 3,406,289 to Schleusener). In addition, particle size measurement utilizing an open cavity laser is shown and described in my U.S. Pat. No. 4,571,079, and by a passive cavity in my U.S. Pat. No. 4,594,715.

Refinements in extinction particle size measurement utilizing open cavity laser devices have also been heretofore described by R.G. Knollenberg and B. Schuster in "Detection and Sizing of Small Particles in Open Cavity Gas Lasers", Applied Optics, Volume 11, No. 7, November, 1972, pages 1515–1520.

Submicron particle sizing devices utilizing light scattering in an open cavity laser device has also been heretofore described by R.G. Knollenberg in "An Active Scattering Aerosol Spectrometer", Atmospheric Technology, Number 2, June, 1973, pages 80–81. Refinements have been described by R.G. Knollenberg in "Active Scattering Aerosol Spectrometry", National Bureau of Standards Special Publication 412, issued October, 1974, pages 57–64; by R.G. Knollenberg and R.E. Luehr in "Open Cavity Laser Active' Scattering Particle Spectrometry from 0.05 to 5 Microns", Fine Particles, Aerosol, Generation measurement, Sampling and Analysis, Editor Benjamin Y.H. Liu, Academic Press, May, 1975, pages 669–696; by R.G. Knollenberg in "Three New Instruments for Cloud Physics Measurements: The 2-D Spectrometer, the Forward Scattering Spectrometer Probe, and the Active Scattering Aerosol Spectrometer", American Meterological Society, International Conference on Cloud Physics, July, 1976, pages 554–561; by R.G. Knollenberg in "The Use of Low Power Lasers in Particle Size Spectrometry", Proceedings of the Society of Photo-Optical Instrumentation Engineers: Practical Applications of Low Power Lasers, Volume 92, August, 1976, pages 137–152; by R.G. Knollenberg in "In Situ' Optical Particle Size Measurements in Liquid Media" presented at Semiconductor Purewater Conference, Palo Alto, California, Jan. 13–14, 1983; and by R.G. Knollenberg in "The Measurement of Particle Sizes Below 0.1 Micrometers", Journal of Environment Science, January-February, 1985.

A linear array of detectors has also heretofore been utilized in conjunction with parallel processing of the electrical signals generated by each detector to achieve data acquisition (see, for example, my U.S. Pat. No. 3,941,982). A highly sensitive particle size detection device using an array of detectors in conjunction with parallel processing is described and claimed in my now pending U.S. pat. application Ser. No. 851,477 (which is the parent application with respect to this application), and is also described in my paper entitled "Sizing Particles At High Sensitivity In High Molecular Scattering Environments" appearing in Proceedings of Institute Of Environmental Sciences, meeting held May 1987 at San Jose, California.

Known particle measuring devices have been heretofore utilized for a variety of purposes, including determining the presence and/or size of particles in various gases, including air. With particular respect to airborne particles, tolerance limitations and the effects of particulate contamination from the environment has made it necessary to utilize effective contamination control in order to enable fabrication of many of the devices now in use. In particular, precision manufacturing, such as is required, for example, for microelectronic systems, has largely been made possible by the development and application of clean rooms and clean devices.

For many years, standard clean rooms of Class 100 or Class 1000 were more than adequate for essentially all of the electronic devices in use. However, when the present generation of microcomputers came into use, the need for micro electronic components, such as large capacity memory chips, has resulted in the development of devices that are extremely susceptible to contamination during manufacturing.

The effects of particulate contamination during fabrication of such devices is that the yield of usable product is greatly reduced. The contamination particles an, for example, interfere with lithographic imaging integrity, or they can result in either open or short circuits, and poisoned domains, depending on their nature. At this time, microchip manufacture appears to be the most critical operation in the electronics manufacturing industry that is affected by particulate contamination.

The semiconductor VLSI (Very Large Scale Integrated Circuit) industry has continued to push the state-of-the-art in air particle counters used to certify clean rooms. The need for much higher standards reflects the demands of the VLSI circuit manufacturer as well as filtration improvements that achieve much lower levels of contamination.

Most now known aerosol counters have one cubic foot per minute (1cfm) sample flow rates. However, to achieve reasonable statistics in a Class 1 environment, it is necessary to sample many cubic feet of air if sensitivity is limited to 0.5 microns ($\mu$m). Since the particle population increases as size decreases, most air particle counter manufacturers have therefore chosen to size much smaller particles to more readily develop the appropriate statistical base.

For example, at 0.1 $\mu$m, the average particle size distribution found in a clean room would provide nearly 100 times as many particle counts $>0.1$ $\mu$m compared to counts $>0.5$ $\mu$m. Thus, the more sensitive the particle counter the less time is required for room standard certification.

In addition, the manufacturers are producing devices with geometries including features that are smaller than 0.5 $\mu$m. Thus, in addition to generating a statistical base in the shortest period of time, higher sensitivity provides known particle size information on more potential defective generators.

With the advent of lasers, the ability to size particles via light scattering as small as 0.1 μm became a routine practice since lasers can have all of their energy focused to a small dimension of high intensity. Several devices now on the market provide 0.1 μm sensitivity but none of these devices are capable of sampling at a 1cfm flow rate, and, in fact, are generally capable of no more than a 0.1 cfm flow rate at 0.1 μm sensitivity Semiconductor manufacturers also require high purity gases with low particulate microcontaminants for a variety of processes. It is necessary to make measurements at line pressures (up to 150 P.S.I.) in most cases. Some of these gases are also high molecular weight gases which scatter more light than air (i.e., a mix of largely oxygen and nitrogen) and thus molecular scattering must be reduced even if flow rates less than 1cfm are adequate.

Thus, the potential statistical advantage at smaller particle size is now partially lost in high molecular scattering environments. A combination which achieves high sensitivity in such an environment (including, for example, achieving a high flow rate of up to or exceeding 1cfm) at high sensitivity (to detect particles having a size at least as small as 0.1 μm) is shown to be achieved in my above-referenced parent application, and such detection has been enhanced by addition of noise cancellation circuitry as described and claimed in this application.

SUMMARY OF THE INVENTION

This invention provides noise cancellation in a particle detection device, and, more particularly, in such a device having high sensitivity in a high molecular scattering environment, with a particle size sensitivity of at least as small as 0.1 micron (0.1 μm) having achieved in such an environment. High sensitivity is achieved at high flow rates (of at least up to one cubic foot per minute), as well as in the presence of high pressure (above atmospheric pressure) or high molecular weight gases.

Background noise due to molecular scattering is reduced, with such noise reduction being effected through use of a plurality of linear detectors, each of which senses a portion of the overall sensing region established at the intersection of the flow path of a mixture of gas and particles and a laser beam and provides an electrical output signal indicative of sensed particles, and with the outputs of all of the detectors being parallel processed with the outputs from detectors monitoring non-adjacent portions of the sensing region being combined through noise cancellation units.

It is therefore an object of this invention to provide an improved particle detection device.

It is another object of this invention to provide an improved highly sensitive particle detection device having noise cancellation.

It is another object of this invention to provide an improved highly sensitive particle detection device with noise cancellation that allows detection of particle sizes at least as small as 0.1 micron in high molecular scattering environments.

It is still another object of this invention to provide an improved particle detection device having a plurality of linear detectors for monitoring a sensing region, and parallel processing of the outputs from the detectors, with noise cancellation circuitry being provided during processing to combine the outputs from detectors monitoring non-adjacent portions of the sensing region.

With these and other objects in view, which will become apparent to one skilled in the art as the description proceeds, this invention resides in the novel construction, combination, and arrangement of parts substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 3 is an illustration of a particle size distribution curve showing actual count data measured in presently constructed clean rooms for the semiconductor very large scale integrated circuit (VLSI) industry;

FIG. 4A is a partial schematic view illustrating a circular flow cross-section utilized to establish a sensing region;

FIG. 4B is a partial schematic view illustrating a rectangularly shaped flow cross-section utilized to establish a sensing region;

FIG. 6 is a simplified side sectional view illustrating positioning of the detector unit for monitoring the sensing region using plural detectors;

FIG. 7 is a simplified electronic schematic and block diagram illustrating parallel processing using plural detectors;

FIG. 8 is a simplified block diagram illustrating the use of cancellation circuitry according to this invention in conjunction with parallel processing as shown in FIG. 7; and FIG. 9 is a simplified electronic schematic illustrating the cancellation circuitry of FIG. 8.

DESCRIPTION OF THE INVENTION

Figure 1:
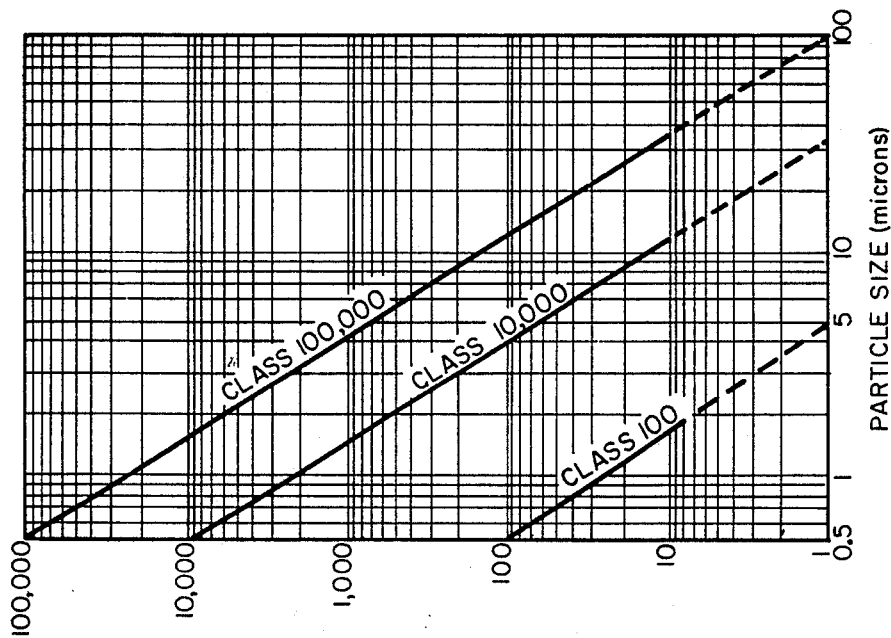
FIG. 1 illustrates a particle size distribution curve according to the classification system and size-concentration ranges as presently set forth in U.S. Federal Standard 209 (FS209)

Present-day particle control in electronic manufacturing areas is based mainly on application of U.S. Federal Standard 209 (FS209), the German VDI 2083 document, or similar standards. FIG. 1 shows the present classification system and the size-concentration ranges used in FS209. Total particles/cubic foot are shown in the left vertical column of FIG. 1 (and also in FIGS. 2 and 3), and, as shown, are equal to and larger than the stated particle size. Counts below 10 (0.35) particles per cubic foot (liter) are unreliable (and hence shown in dotted lines) except when a large number of samplings is taken. As can be seen, the smallest particle that needs to be measured is 0.5 micron in diameter, and the maximum cleanliness level specified is 100 particles per cubic foot.

These clean room standards, however, have been in existence for several years, and present requirements for electronic products have shown that the level covered is not satisfactory for reasonable production of microelectronic devices since particle control requirements have now become more restrictive. The need for revised particle contamination level definitions has therefore become apparent, and, for that reason, plans are under way to modify FS209 to allow measurements to be made including smaller particles and cleaner levels.

While a revision of FS209 is now underway under the direction of the Institute of Environmental Science, this revision is not yet complete. One of the major objectives of the revision is to define a room, or area, air cleanliness class at the Class 10 level, and to permit measurement of particles in sizes below 0.5 micron in diameter so as to allow adequate statistical definitions at the lower levels. It can be expected that the standards used in all industrial areas will also probably soon be revised, and revision of FS209 therefore appears to be only the first in a series of new standards. In fact, Class 1 levels are currently capable of being produced, and must also be addressed in the near future.

Figure 2:
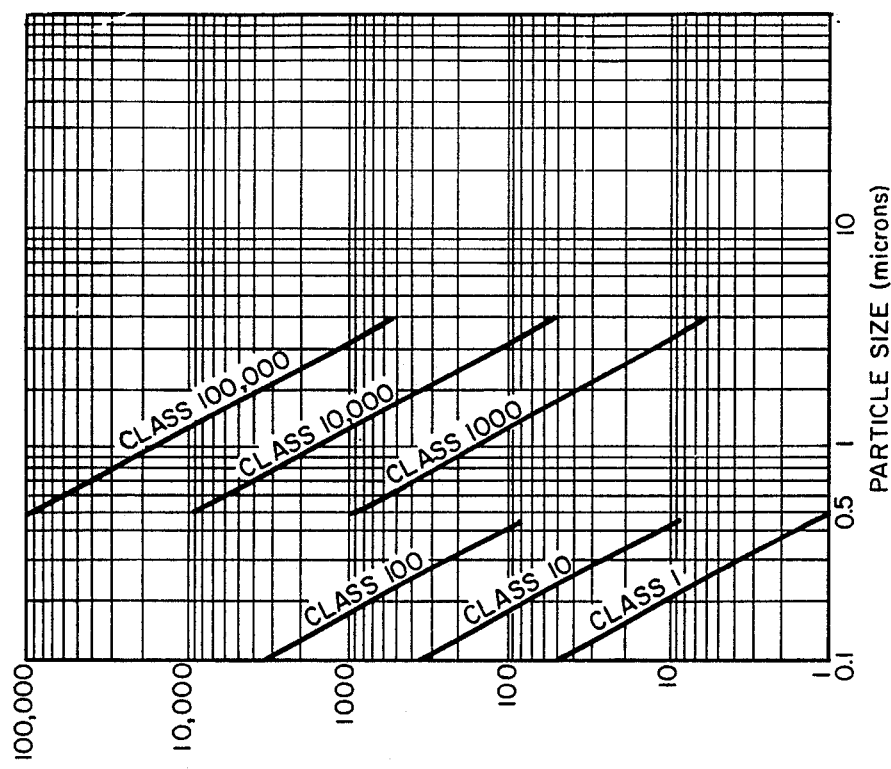
FIG. 2 is an illustration of a particle size distribution curve according to the present planned revision of FS209.

Since particle concentration increases rapidly as particle size decreases, the advisability of measurements of smaller particles appears reasonable. Therefore, plans for the revised FS209 involve measurements at 0.3 $\mu m$, and at 0.1 $\mu m$ for cleaner areas. FIG. 2 shows the presently planned format of the classifications, allowing measurement at sizes below 0.5 $\mu m$. However, it should be noted that the slopes of the classification curves in FIG. 2 are based on the same slopes as in the present FS209.

Consideration is being given to modification of the slopes of the classification curves in accordance with more recent data that have been obtained in a few VLSI clean rooms in the United States. A laser counter was used to measure from 0.1 $\mu m$ up, and the data obtained are shown in FIG. 3. It appears that the particle size distribution in very clean rooms has a much steeper slope below the 1.0 $\mu m$ size than would be expected from the present FS209 classification curves, and there is some possibility of making the slopes steeper as shown in FIG. 3.

If the classification curves are extended to the 0.1 $\mu m$ size range, then the time and effort to obtain valid data for rooms of Class 100 and better will be reduced regardless of whether FS209 is simply extrapolated or revised according to the more recent data of FIG. 3.

Development of a device that can achieve a sensitivity of 0.1 micron in a high molecular scattering environment was not readily achieved. With respect to a molecular scattering environment due to high flow rates of up to, or exceeding one cubic foot per minute, such rates dictate a fairly large cross section of flow passing through the sensitive volume of an optical sensing device.

Even at sonic velocities, the cross-section is 1.8 mm$^2$, and full sonic flow is impossible to achieve by practical vacuum sources. Thus, the more typical flow velocities are $\frac{1}{3}$ to $\frac{1}{2}$ sonic, and the flow cross sections increase to 4-5 mm$^2$ in typical instruments at 1cfm. This large cross-section of flow must be illuminated uniformly if particles are to be sized accurately.

Thus, the illuminated region cannot be near a small focused region of a laser but must ordinarily be placed in an expanded laser beam, if the flow cross section is circular as indicated in FIG. 4(a), or stretched along the beam axis, if the flow cross section is made rectangular as illustrated in FIG. 4(b). Thus, a near optimum design, as utilized herein, has a flow cross section of 1 × 10 mm$^2$ and collecting optics as shown similar to that shown in my in U.S. Pat. Nos. 4,571,079 and 4,594,715.

The laser itself must generate about 1 watt of power within the sensing region in order to produce 0.1 $\mu m$ sensitivity. A resonant HeNe laser cavity operating at 633 nm is the most expedient method of generating the required power, although any 1 watt visible light laser can be used (e.g., argon ion). Thus, since light sources can be devised to provide the energy density sufficient to sense particles as small as 0.1 $\mu m$ and enable cross-sections permitting 1cfm, the problem would appear to be straightforward.

This would have been the case if the particles were the only source of light scattering within the sensing region. By careful design, stray light can be effectively eliminated. However, there are approximately 10$^{16}$ air molecules per cubic mm accompanying the airborne particles as they transit the laser beam and these air molecules cannot be eliminated. Calculations show that such a volume of air scatters over 100 times more energy than a typical 0.1 $\mu m$ particle (see "The Measurement of Particle Sizes Below 0.1 Micrometers" by R.G. Knollenberg appearing the The Journal of Environmental Sciences, January-February, 1985). Since the large ensemble of molecular scatterers is ever present, this signal source is largely d.c.

It is the variations (a.c.) in the molecular scattering signal (a.c. noise) that mask the desired 0.1 $\mu m$ particle signal. This noise is itself proportional to the d.c. molecular scattering signal. If the noise source is classical Shott noise, it is proportional to the square root of the d.c. signal. However, with laser sources, the noise is higher than calculated by the Shott noise assumption, and laser cavities are easily randomly modulated (generating noise) by the flow itself. In such cases, the a.c. noise is directly proportional to the d.c. component instead of the square root. Measurements reveal that in most 1cfm systems the molecular scattering noise is 5 to 10 times that of a 0.1 $\mu m$ particle, making detection impossible with known devices.

A high molecular scattering environment, or background, exists, for example, when molecular scattering can exceed the 0.1 micron particles scattered by one hundred times. Such high molecular scattering can be generated, not only when the gas volume being viewed is large as is required for high flow rates, but also can be generated, for example, due to high molecular density (high pressures above ambient) or due to the presence of large gas molecules. In any case, whenever a high molecular scattering background in encountered, the device of this invention can be utilized to enable high sensitivity to be achieved in the presence of the high molecular scattering background.

Figure 5:
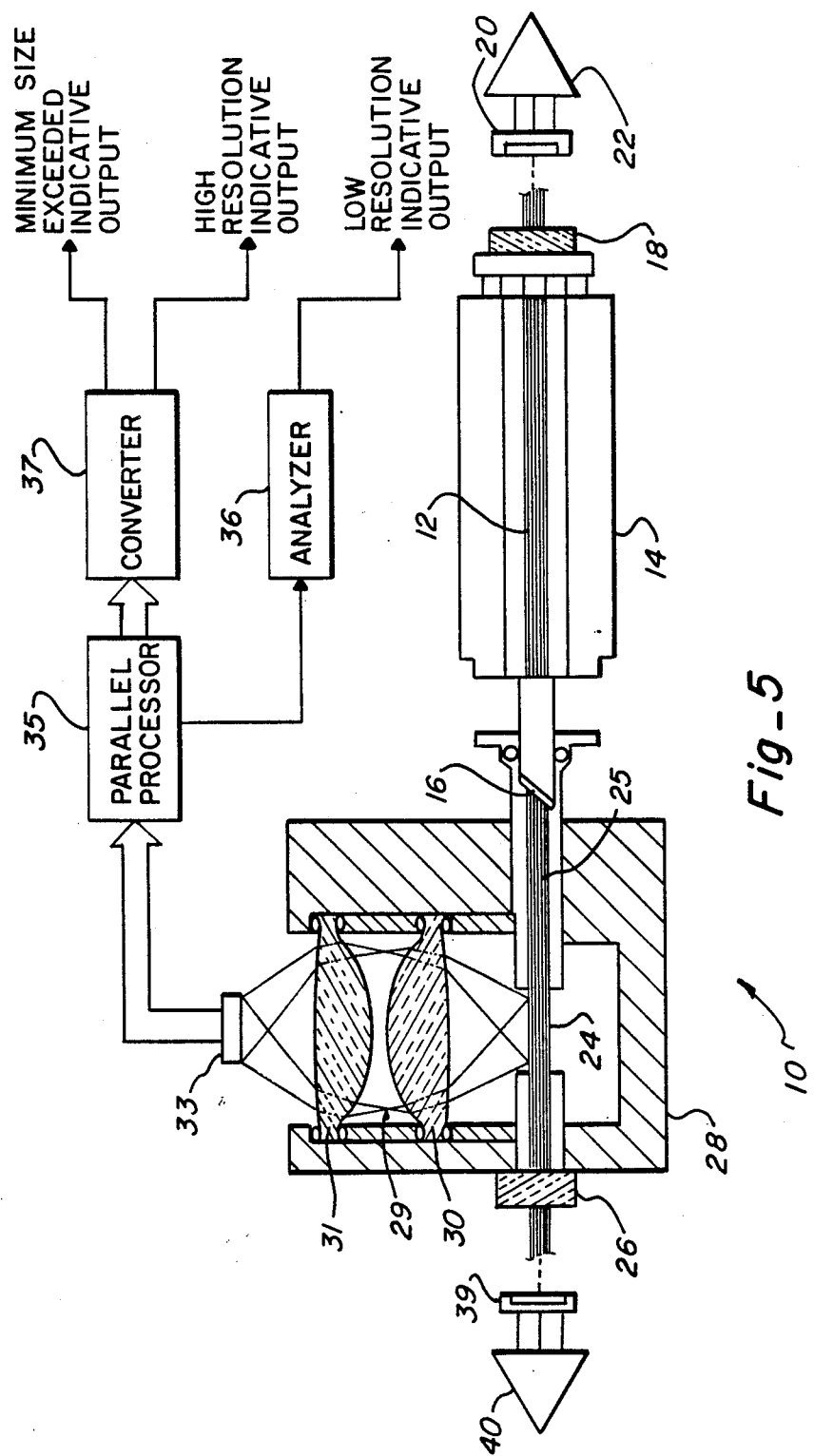
FIG. 5 is a simplified side section view schematic presentation of a particle size measuring device having an open cavity laser and having parallel processing utilized in conjunction therewith.

An illumination system is utilized herein to illuminate a sensing region, or volume, through which a gas (usually air), having the particles to be sensed therein, is caused to flow. The illumination system is preferably, as indicated in FIG. 5, a laser beam illumination system 10, such as is shown in my U.S. Pat. Nos. 4,571,079 and 4,594,715.

As shown in FIG. 5, access to laser cavity 12 can be gained by terminating plasma tube 14 at one end with a Brewster's window 16. A curved mirror 18 (with radius r=100 cm, for example) is positioned at the other end of tube 14. A photodetector 20 and preamplifier 22 are conventionally positioned along the laser beam axis outside mirror 18 to provide a measure of relative intensity of illumination.

For particle size measurement, particles to be size measured are injected through jets 24 so that the particles pass through laser beam 25 between the Brewster's window 16 and an external laser mirror 26 (with r=70 cm, for example).

As shown in FIG. 2, optical sampling block 28 is positioned adjacent to the particle injection area, and block 28 positions light collecting optical elements, or imaging system, 29, which system may include, as shown, a pair of lenses 30 and 31, above and close to the particle injection area.

A photodetector unit 33, having a plurality of detectors 34 (as indicated in FIGS. 6 and 7), is positioned adjacent to block 28, so that photodetector unit 33 is located in the focal plane of lenses 30 and 31. The electrical signal outputs from photodetector unit 33 is coupled to parallel processor 35. The output of parallel processor 35 may be coupled through analyzer unit 36 to provide a low resolution indicative output, and is coupled through converter unit 37 to provide a digital particle size high resolution indicative output. In addition, a minimum size exceeded indicative output is also provided from converter unit 37.

Photodetector 39 and preamplifier 40 may be optionally positioned along the laser beam axis at the other side of mirror 26 to provide a reference measurement, as does photodetector 20 and preamplifier 22.

Noise can be reduced by using an imaging system and detector array to reduce the background light from molecular scattering to manageable levels. As shown best in FIG. 6, detector unit 33 includes a linear array of rectangular elements, or detectors, 34 (eleven of which are indicated in FIG. 6 for illustration purposes). The use of a linear array of detectors connected to parallel processing circuitry for two-dimensional data acquisition is described in my U.S. Pat. No. 3,941,982.

This array of elements (which may be photodiodes as indicated in FIG. 7) view corresponding volumes (i.e., a portion of the entire sensing region) within the laser beam. Light scattered from a particle is reimaged onto a single element as a bright image along with a background of diffuse molecular scattering produced by all of the air molecules in a particular element's monitored portion of the overall sensing region.

Thus, the amount of background molecular scattering is reduced by the number of elements selected for the array. For light noise sources other than those described by Shott noise, there is also a direct reduction in noise proportional to the number of array elements. For Shott noise sources, the noise reduction is proportional to the square root of the number of array elements.

Since there are N independent detectors utilized in this invention, the electrical signal output from each must be individually interrogated to determine when a particle image has been observed by any on element. FIG. 7 illustrates a plurality of detectors 34 forming detection unit 33, with each detector being connected to a different signal processing circuit 41 of parallel processor 35. More particularly, each detector 34 is connected with preamplifier 42 (each of which amplifiers has a feedback resistor 43 connected between the output and the negative input) in each signal processing circuit 41. Each processing circuit 41 also includes a comparator 44 and a peak storage element (sample and hold circuit) 46.

Each preamplifier 42 develops an amplified electrical signal of the noise and particle event, which signal is coupled to the comparator 44 associated therewith. The threshold level of the comparator is set at the signal peak amplitude of the minimum detectable particle size. The comparator outputs are OR'ed together through control logic unit 48 which provides a particle transit time pulse for timing purposes and an indication of when a particle of minimum detectable size has been detected.

For sizes larger than the minimum detectable size, resolving the size depends upon the amount of resolution desired. If a simple count of all particles >0.1 $\mu$m in a single size channel is desired, for example, signal processing circuits 41 may simply be utilized in combination with control logic unit 48.

For high resolution multi-channel applications (e.g., where 0.01 $\mu$m resolution is desired with 10 channels between 0.1 $\mu$m and 0.2 $\mu$m), it is necessary to individually store the peak amplitudes of each detector prior to processing. For such high resolution (e.g., where the second threshold is at 0.11 $\mu$m), the output from each preamplifier 42 is coupled to its associated peak storing unit (sample and hold circuit) 46 which stores the peak amplitude. The peak amplitudes stored in sample and hold circuits 46 are then individually read out by converter unit 37, which includes control logic unit 48 and scanning A/D converter 49 (as indicated in FIG. 7).

For low resolution multi-channel applications, it is sufficient to sum all of the outputs from amplifiers 42 by coupling each output through an associated resistor 50 to summing amplifier 52 (which has a feedback resistor 53 connected between the output and the negative input) of analyzer unit 36, which unit also includes a conventional pulse height analyzer 54 to receive the outputs from amplifier 52. Such a low resolution application implies that the second threshold level to be used is sufficiently higher than the first such that the summed noise is still smaller than peak amplitudes which exceed the second threshold level. For example, if the second threshold is 0.2 $\mu$m, it would be about 40× greater than the 0.1 $\mu$m threshold, and the summed noise would be much less than such a high threshold.

Each signal processing circuit, in conjunction with its associated detector, thus determines when a particle event has occurred and the magnitude of the scattering event, which can be shared between two elements when the image is at the boundary or slightly out of focus.

It has now been found that still further improvement of detection can be achieved by incorporating noise cancellation circuitry in the parallel processing arrangement shown in FIG. 7.

As illustrated in FIG. 8, noise cancellation circuitry 58 consists of a plurality of cancellation units 60 (designated in FIG. 8 as units 60a and 60b) each of which is connected to receive the outputs from detectors that monitor spaced, or non-adjacent, portions of the entire region sensed by the detection unit utilized.

As indicated in FIG. 6, detection unit 33 includes a plurality of detectors arranged so that each area monitored by each detector covers a portion of the entire sensing area with each area thus having some other areas adjacent thereto and the remainder of the other areas spaced, or non-adjacent, thereto.

As indicated in FIG. 8, detector 34a monitors an area adjacent to the area monitored by detector 34b but is spaced, or non-adjacent, to the area monitored by detector 34c. In like manner, detector 34b monitors an area adjacent to the area monitored by detector 34c but is spaced, or non-adjacent, with respect to the area monitored by detector 34d, and detector 34c monitors an area adjacent to the area monitored by detector 34d.

While only four detectors are illustrated in FIG. 8, it is to be realized that this pattern is carried out by all detectors utilized, and that pairs, or groups, of detectors monitoring spaced, or non-adjacent, areas can be readily selected for noise cancellation.

As also shown in FIG. 8, the output from detector 34a is coupled through preamplifier 42a to cancellation unit 60a, while the output from detector 34c (i.e., the detector monitoring a non-adjacent area with respect to the area monitored by detector 34a) is coupled through preamplifier 42c to cancellation unit 60a. In like manner, the output from detector 34b is coupled through preamplifier 42b to cancellation unit 60b, and the output from detector 34d (i.e., the detector monitoring a non-adjacent area with respect to the area monitored by detector 34b) is coupled through preamplifier 42d to cancellation unit 60b (it is to be realized that the number of cancellation units will normally be one-half that of the total number of detectors utilized).

After noise cancellation occurs at the cancellation units, the remaining signal is coupled to the particle determining circuits. As shown in FIG. 8, the output from cancellation 60a is therefore coupled to comparator 44a, sample and hold circuit 46a, and through resistor 50a to analyzer unit 36, while the output from cancellation unit 60b is coupled to comparator 44b, sample and hold unit 46b and through resistor 50b to analyzer unit 36 (all of which are described above in connection with FIG. 7).

FIG. 9 illustrates the specific circuitry of cancellation unit 60a (it is to be realized that the other cancellation units 60 utilized would be identical). As shown, the output from detector 34a is coupled through preamplifier 42a to resistor 62 of cancellation unit 60a, while the output from detector 34c is coupled through preamplifier 42c to inverter 64 of cancellation unit 60a, with the output of inverter 64 being coupled to resistor 66. Resistors 62 and 66 are connected for summing the outputs from the detectors, with the summed output being then coupled from summing junction 68 to comparator 44a, sample and hold unit 46a and through resistor 50a to analyzer unit 36.

As also illustrated in FIG. 9 by way of example, if output A (from detector 34a) includes both noise and signal, and if output B (from detector 34c) includes only noise, then the noise of the inverted B output ($\overline{B}$ as indicated in FIG. 9) will cancel the noise in the A output when summed by the cancellation unit (i.e, $A + \overline{B} = 0$).

Common mode noise does not correlate from points along the beam that are separated very far (i.e., greater than a few mm). While a problem exists for all beams, the problem is most severe for high order multimode lasers where coherence length is short. Since the degree of correlation relates to the spatial phase coherence along the beam axis, if samples are taken at small separations in distance, the coherence is greatly improved and the noise correlates. Therefore, by using an array of detectors 34 to sample short distances, and then inverting the output from one of a pair of detectors, noise cancellation is achieved according to this invention (it should be noted that detectors monitoring adjacent areas cannot be paired because images can be shared between the two adjacent detectors).

In operation, a laser beam is directed through the sensing region and a medium (normally gas, although a fluid or a solid may be utilized) having particles therein is caused to flow through the sensing region at flow rates that can include a flow of at least about 1cfm. Particles within the sensing region cause light scattering, with such light scattering due to particles having a diameter down to at least 0.1 $\mu$m and larger being detectable by the array of detectors. Each detector of the array of detectors monitors a predetermined volume of the sensing region, senses detectable light scattering within the monitored portion, and provides an electrical output signal indicative of sensed light scattering (along with signals caused by background noise). The electrical output signals are parallel processed and the outputs from each pair of detectors monitoring non-adjacent areas are combined in noise cancellation units, after which the outputs from the cancellation units are further processed in particle determining circuitry.

In a working embodiment utilizing the circuitry of FIGS. 7, 8 and 9, a particle size sensitivity of 0.1 micron has been achieved in a high molecular scattering environment represented by a flow rate of 1 cubic foot per minute.

This invention thus provides an improved particle size detection device that is capable of achieving high sensitivity using of an array of detectors and noise cancellation circuitry.

What is claimed is:

1. In a particle size detection device having first means for enabling a medium having particles therein to be passed through a predetermined sensing region and second means for illuminating said sensing region so that particles in said sensing region cause light scattering, an improved particle sensing system comprising:

detecting means for receiving and detecting light scattered at said sensing region, said detecting means including a plurality of detectors positioned so that predetermined ones of said detectors receive light scattered from predetermined portions of said sensing region, with said predetermined portions of said sensing region being spaced with respect to one another, and with each of said detectors providing an output that can include both noise and signals indicative of sensed light scattered by particles within said predetermined portion of said sensing region monitored by that detector; and processing means including noise cancellation means connected with said predetermined ones of said detectors, said noise cancellation means causing noise included in said outputs from said predetermined ones of said detectors to be substantially cancelled so that the output from said processing means is effectively indicative of said particles causing said light scattering in said sensing region.

2. The system of claim 1 wherein said sensing region includes a high molecular background, and wherein said system enables effective operation of said device in the presence of said high molecular scattering background.

3. The system of claim 1 wherein said detecting means senses particles having a diameter of about 0.1 micron and larger, and wherein said processing means enable effective detection and processing of light scattered by particles within said sensing region with said particles having a diameter of at least as small as 0.1 micron and larger.

4. The system of claim 1 wherein said first means includes means for passing said medium with particles therein through said sensing region at a rate of at least about 1 cubic foot per minute, and wherein said detecting means and said processing means enable effective detection and processing of light scattered by particles within said sensing region having said flow of said medium including said particles through said sensing region at a rate of at least about 1 cubic foot per minute.

5. The system of claim 1 wherein said processing means is a parallel processor that includes a plurality of processing circuits each of which is connected with a different one of said predetermined ones of said plurality of detectors to separately process the outputs therefrom, and with the outputs of said processing circuits being connected with said noise cancellation means.

6. The system of claim 1 wherein said noise cancellation means includes a plurality of noise cancellation units each of which is connected with a pair of predetermined ones of said detectors.

7. The system of claim 6 wherein each of said noise cancellation units includes summing means and signal inverter means connected with one of said predetermined ones of said detectors to invert the output therefrom prior to coupling said output to said summing means.

8. The system of claim 1 wherein said plurality of detectors include second predetermined ones positioned to receive light from second predetermined portions of said sensing region, with each of said second predetermined portions being spaced with respect to one another and adjacent to said first predetermined portions of said sensing region, and wherein said processing means includes second noise cancellation means connected with said second predetermined ones of said detectors to cause noise cancellation in the outputs thereof.

9. The system of claim 8 wherein said detecting means receives and detects light scattered over substantially said entire sensing region with said predetermined portions and said second predetermined portions of said sensing region being alternated.

10. In a particle size detection device having first means for enabling a medium including particles therein to be passed through a predetermined sensing region and second means for illuminating said sensing region so that particles in said sensing region cause light scattering, an improved particle sensing system comprising:
   detecting means for receiving and detecting light scattered by said particles in said medium passed through said sensing region, said detecting means including a plurality of pairs of detectors each of which detectors monitors a predetermined different portion of said sensing region with said portion monitored by each detector of each said pair of detectors being spaced with respect to one another, and with each of said detectors providing an electrical signal output indicative of sensed light scattered by particles in said portion of said sensing region monitored by that detector;
   a plurality of signal processing means each of which is connected with a different one of said detectors to separately receive the electrical signal output therefrom and providing an output indicative of the electrical signal output received from said detector associated therewith; and
   cancellation means including cancellation units connected with different ones of each of said pairs of detectors through said signal processing means to receive the outputs therefrom and responsive thereto substantially cancelling noise in said outputs so that the output from said system is effectively indicative of particles causing light scattering within said sensing region.

11. The system of claim 10 wherein each of said plurality of signal processing means includes amplifying means connected between said detectors and said cancellation units.

12. The system of claim 10 wherein said cancellation means includes a plurality of cancellation units equal in number to the number of said pairs of detectors.

13. The system of claim 12 wherein each of said cancellation units includes summing means and inverting means for providing an inverted output from one detector of said pair of detectors to said summing means.

14. A particle size detection device capable of operating with high sensitivity at high flow rates, said device comprising:
   conduit means providing a flow path for a mixture of particles and gas through a predetermined sensing region with the capacity of flow of said mixture through said sensing region including a rate of at least about one cubic foot per minute;
   laser means providing a laser beam passing through said sensing region;
   imaging means positioned adjacent to said sensing region;
   a plurality of detectors first and second groups of each of which are adapted to monitor different portions of said sensing region through said imaging means and sense light scattered at said sensing region by particles within said portion of said sensing region, with each of said portions monitored by each of said first and second groups of detectors being spaced with respect to portions monitored by other detectors of each said group, and with each of said detectors sensing particles having a diameter of about 0.1 micron and larger and providing an electrical signal output indicative thereof;
   a plurality of signal processing circuits each of which includes an amplifier connected with a different one of said plurality of detectors;
   noise cancellation means including a plurality of cancellation units each of which is connected with different ones of at least two of said detectors of a said group through said amplifier connected with said detector, each of said noise cancellation units including a first resistor connected with one of said amplifiers, an inverter connected with a different one of said amplifiers, a second resistor connected with said inverter, and a summing junction connected to said first and second resistors; and
   particle determining means connected with said summing junctions for receiving outputs therefrom and responsive thereto providing an effective indication of particles sensed over said entire sensing region monitored by said plurality of detectors.

15. The device of claim 14 wherein said particle determining means includes at least one of comparator means, sample and hold means, and analyzer means.

* * * * *